US007056281B2

(12) United States Patent
Bookwalter et al.

(10) Patent No.: US 7,056,281 B2
(45) Date of Patent: Jun. 6, 2006

(54) PHALLIC DEVICE MOUNT AND METHOD OF USE

(76) Inventors: Dale M. Bookwalter, 33809 SE. Eastgate Cir., Corvallis, OR (US) 97333; Rhonda S. Bookwalter, 33809 SE. Eastgate Cir., Corvallis, OR (US) 97333

( * ) Notice: Subject to any disclaimer, the term of this patent is extended or adjusted under 35 U.S.C. 154(b) by 0 days.

(21) Appl. No.: 10/850,287

(22) Filed: May 19, 2004

(65) Prior Publication Data

US 2005/0143621 A1 Jun. 30, 2005

Related U.S. Application Data

(60) Provisional application No. 60/532,501, filed on Dec. 24, 2003.

(51) Int. Cl.
*A61F 5/00* (2006.01)

(52) U.S. Cl. ........................................................ 600/38

(58) Field of Classification Search ............ 600/38–41; 128/845, 846, 870; 5/633, 634, 610, 615, 5/651; 606/244; 297/377
See application file for complete search history.

(56) References Cited

U.S. PATENT DOCUMENTS

| | | | | |
|---|---|---|---|---|
| 4,515,361 | A * | 5/1985 | Melillo et al. | 482/140 |
| 4,550,907 | A * | 11/1985 | Melillo et al. | 482/140 |
| 5,016,617 | A * | 5/1991 | Tarlow et al. | 601/117 |
| 5,170,983 | A * | 12/1992 | Stewart | 248/558 |
| 6,203,491 | B1 * | 3/2001 | Uribe | 600/38 |
| 6,311,942 | B1 * | 11/2001 | Rotter et al. | 248/316.5 |
| 2002/0018601 | A1 * | 2/2002 | Nelson | 383/7 |
| 2004/0129274 | A1 * | 7/2004 | Espinosa | 128/845 |

* cited by examiner

*Primary Examiner*—Samuel G. Gilbert
(74) *Attorney, Agent, or Firm*—Ipsolon llp

(57) ABSTRACT

A phallic device mount for operably securing a phallic device thereto and a method of use are disclosed. The mount is positioned adjacent to and supported by a bed. A substantially planar bed-engaging portion is positioned below the mattress of the bed and extends to the mount thereby holding the mount in place during use. Preferably, the substantially planar bed-engaging portion is retractable within the mount for easy concealment of the mount when not in use, and it is slideably secured between a box spring and mattress of the bed during use of the mount. In a preferred embodiment, the height of the planar bed-engaging portion and the height of the phallic device are both independently adjustable by a user.

19 Claims, 4 Drawing Sheets

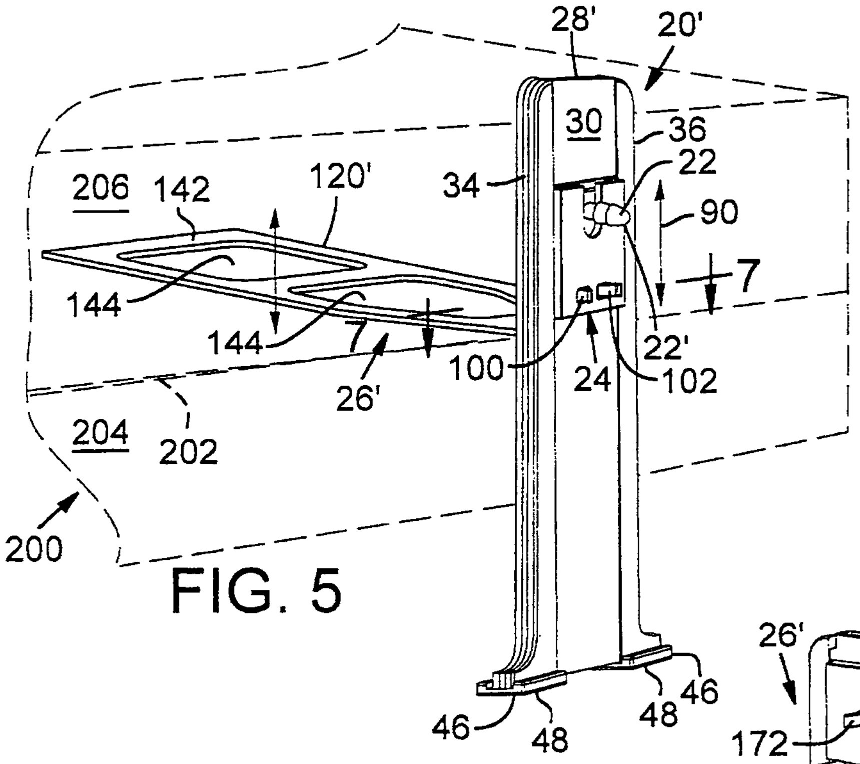
FIG. 5
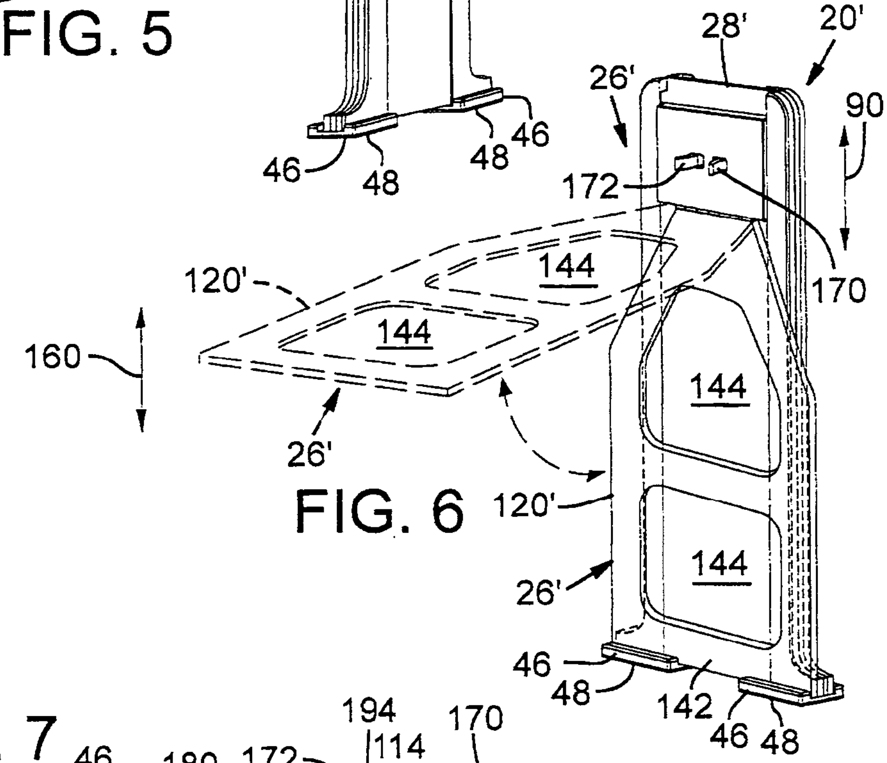
FIG. 6
FIG. 7
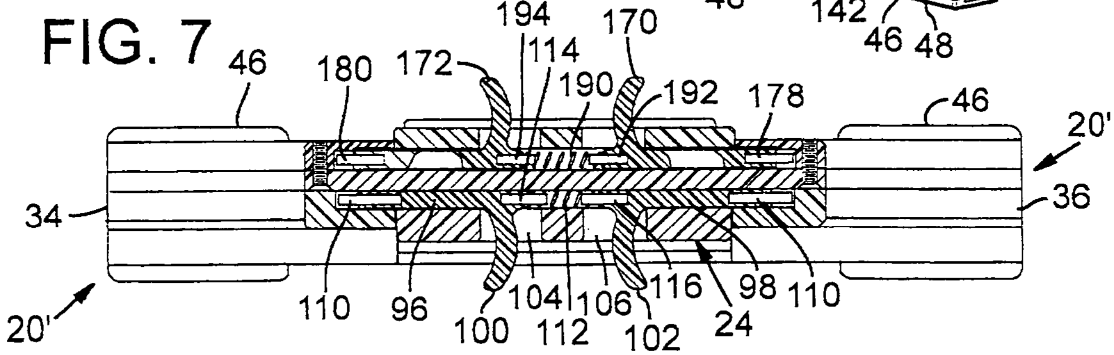

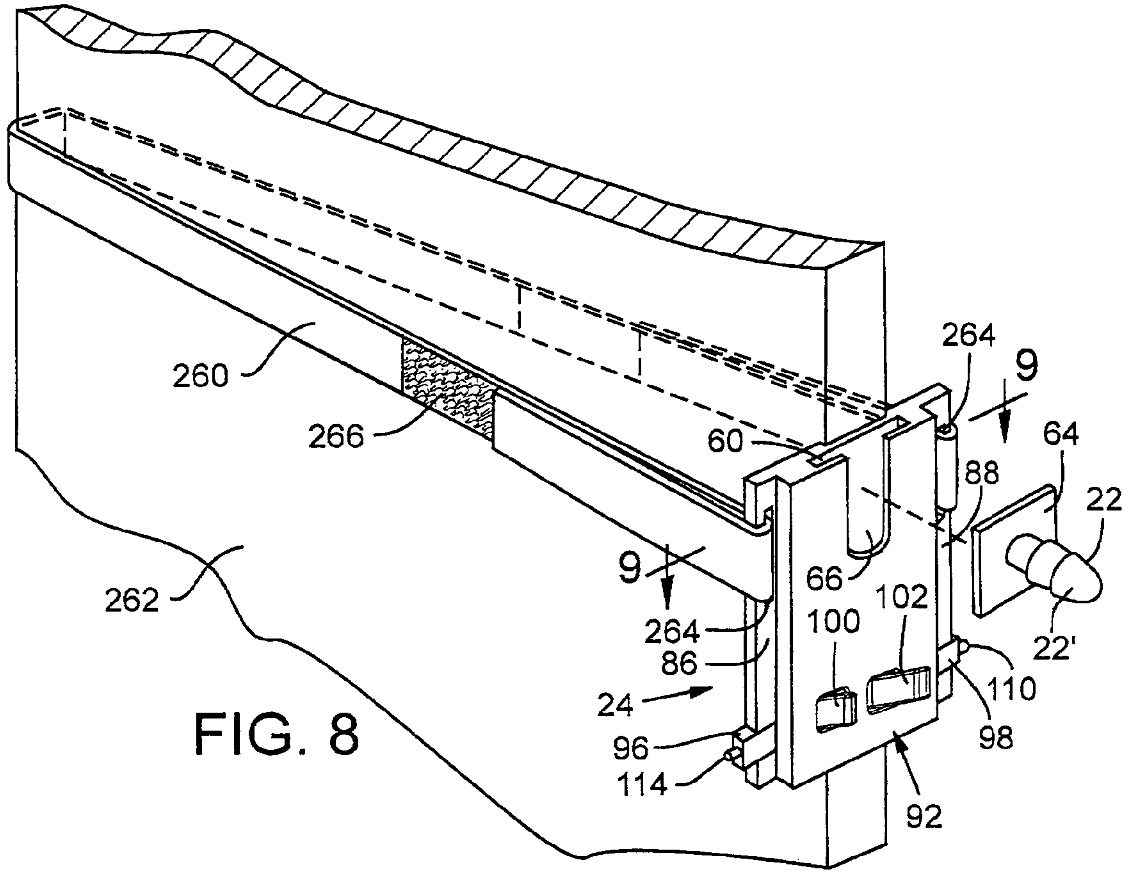
FIG. 8
FIG. 9
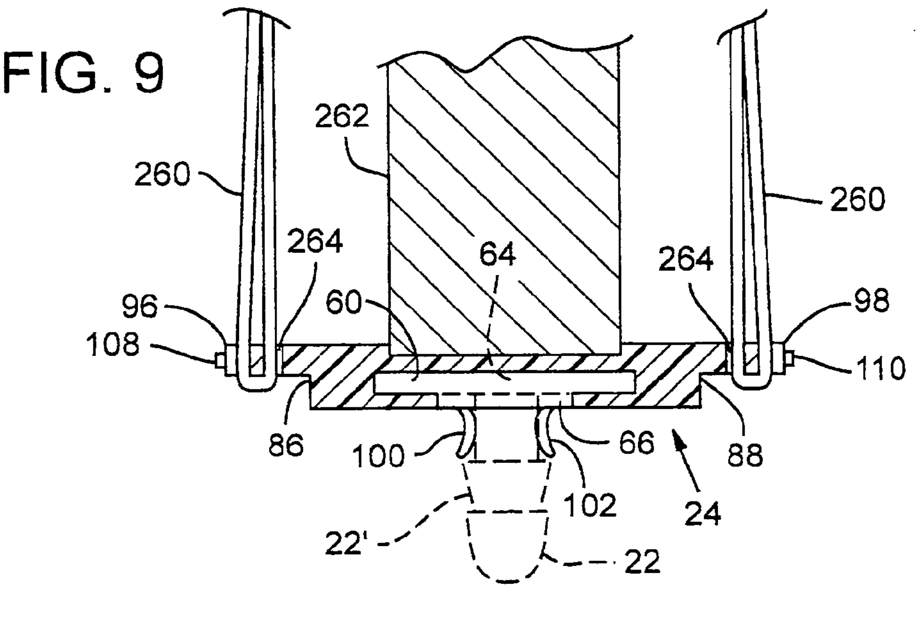

PHALLIC DEVICE MOUNT AND METHOD OF USE

CROSS-REFERENCE TO RELATED APPLICATIONS

This application claims priority to U.S. Provisional Patent Application No. 60/532,501 filed on Dec. 24, 2003.

TECHNICAL FIELD

This invention relates to the field of mounting structures for phallic devices such as penis substitutes, elongate sexual devices, dildos, vibrators, and the like.

BACKGROUND OF THE INVENTION

Phallic devices have been used for many years primarily for sexual pleasure both by couples and by people who do not have a sex partner. The phallic device is an elongate object sized and shaped to be inserted into the vagina of a woman and/or the anus of a person. Usually, phallic devices are either a smooth edged contoured cylinder or they are shaped to resemble either an erect or flaccid human penis. More recently, modern fabrication methods and materials allow phallic devices to be formed into any shape, size, or texture.

The use of phallic devices for obtaining sexual pleasure is gaining popularity along with social acceptance. This increased popularity is due to a number of social and environmental factors including: 1) an increase in sexually transmitted diseases such as AIDS and the like; 2) an increasingly open attitude towards human sexuality within our society; and 3) a desire for couples and people who do not have a sex partner to privately and safely explore a wide variety of sexual experiences.

Despite increasing social acceptance of phallic devices, most users prefer to keep them, and any related structures associated with using them, concealed when not in use.

Historically, most phallic devices are held by the user themselves or by a sexual partner during use. Unfortunately, the number of sexual activities that may be simulated or performed by a user is necessarily limited by the phallic device holders' reach and the holder's range of movement available. Moreover, physically challenged individuals may not have the capacity to properly hold the phallic device for use. Accordingly, their ability to enjoy the benefits of these devices is limited.

Recently, efforts have been made to provide hands-free use of phallic devices. For example, U.S. Pat. No. 5,690,604 to Barnett ("Barnett") discloses mounting a phallic device to a C-shaped clamp. The C-shaped clamp may then be secured by a user to a support structure, such as a bedpost or the like. Similarly, U.S. Pat. No. 5,127,396 to McAllister ("McAllister") discloses mounting a phallic device to a universal mount. The universal mount may then be strapped around a wearer's torso, thereby allowing the wearer to insert the phallic device into their partner and simulate thrusting movements normally associated with performing the sexual act.

Despite the benefits offered by these types of phallic device mounting structures, they have several drawbacks. For example, a hand-tightened clamp on a bed frame is often insufficient to withstand the forces generated during use of the phallic device. Accordingly, the phallic device may tend to move or detach from the bed frame during use. Such movement can damage the bed frame, or worse yet; injure a user.

Moreover, the mounting structure in Barnett requires a user to have a suitably sized support structure for engaging the C-shaped clamp positioned at substantially the same height where the phallic device must be positioned for use. In practice, this positioning for the support structure is difficult to find in a suitably private environment sufficient for using the phallic device therein.

Similarly, while the strap on mounting structure in McAllister may offer sexual partners an opportunity to engage in a new sexual experience together, it does not allow hands free use of the phallic device by a single user. Also, both the C-shaped clamp in Barnett and the strap on mounting structure in McAllister are not particularly aesthetically pleasing, nor do they allow for easy concealment and storage when not in use.

SUMMARY OF THE INVENTION

Accordingly, despite the available phallic device mounting structures, there remains a need for an adjustable phallic device mount that provides hands-free use of the phallic device, that is easy to assemble, adjust and use, and provides rigid support for the phallic device during use, and that may be easily concealed and stored when not in use. In addition to other benefits that will become apparent in the following disclosure, the present invention fulfills these needs.

The invention is a phallic device mount for operably securing a phallic device thereto. The mount is positioned adjacent to and supported by a bed. A substantially planar bed-engaging portion is positioned below the mattress of the bed and extends to the mount thereby supporting the mount during use. Preferably, the substantially planar bed-engaging portion is retractable within the mount for easy concealment when not in use. In a preferred embodiment, the height of the planar bed-engaging portion and the height of the phallic device are both independently adjustable by a user.

BRIEF DESCRIPTION OF THE DRAWINGS

FIG. 5 is an isometric, front view of a phallic device mount in accordance with an alternative embodiment of the present invention showing a possible in-use position and a possible orientation with respect to a bed.

FIG. 6 is an isometric, back view of the phallic device mount structure of FIG. 5 showing possible movement of a bed-mounting portion.

FIG. 7 is a cross sectional view of the phallic device mount of FIG. 5 taken along line 7—7 of FIG. 6.

FIG. 8 is an isometric view of a phallic device mounting portion of an embodiment of the present invention used in a possible alternative mounting to an auxiliary support structure in accordance with an embodiment of the present invention.

FIG. 9 is a section view of the phallic device mounting portion of FIG. 8 taken along line 9—9 of FIG. 8.

DETAILED DESCRIPTION

A mount 20 for a phallic device 22 is shown in FIGS. 1–7. The mount 20 preferably includes a height adjustable phallic device mounting portion 24 and a height adjustable bed-mounting portion 26.

A. General Assembly

Figure 1:
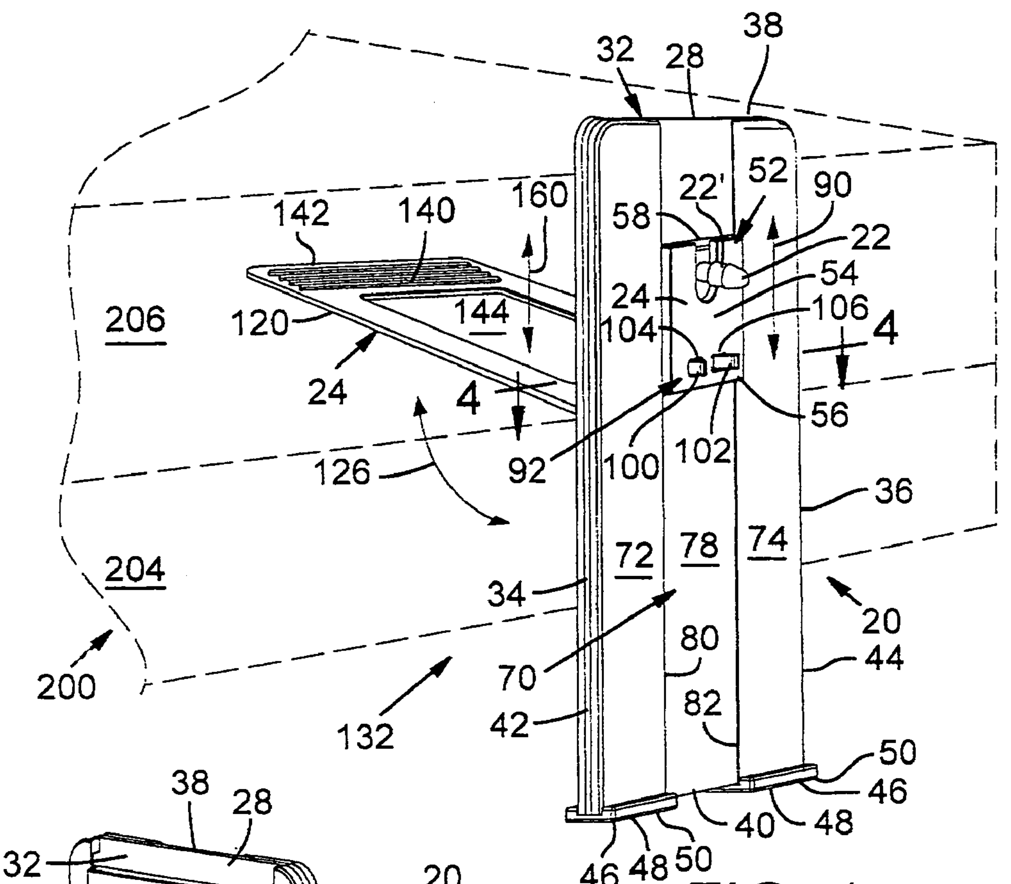
FIG. 1 is an isometric, front view of a phallic device mount in accordance with an embodiment of the present invention showing a possible in-use position and a possible orientation with respect to a bed.
Figure 3:
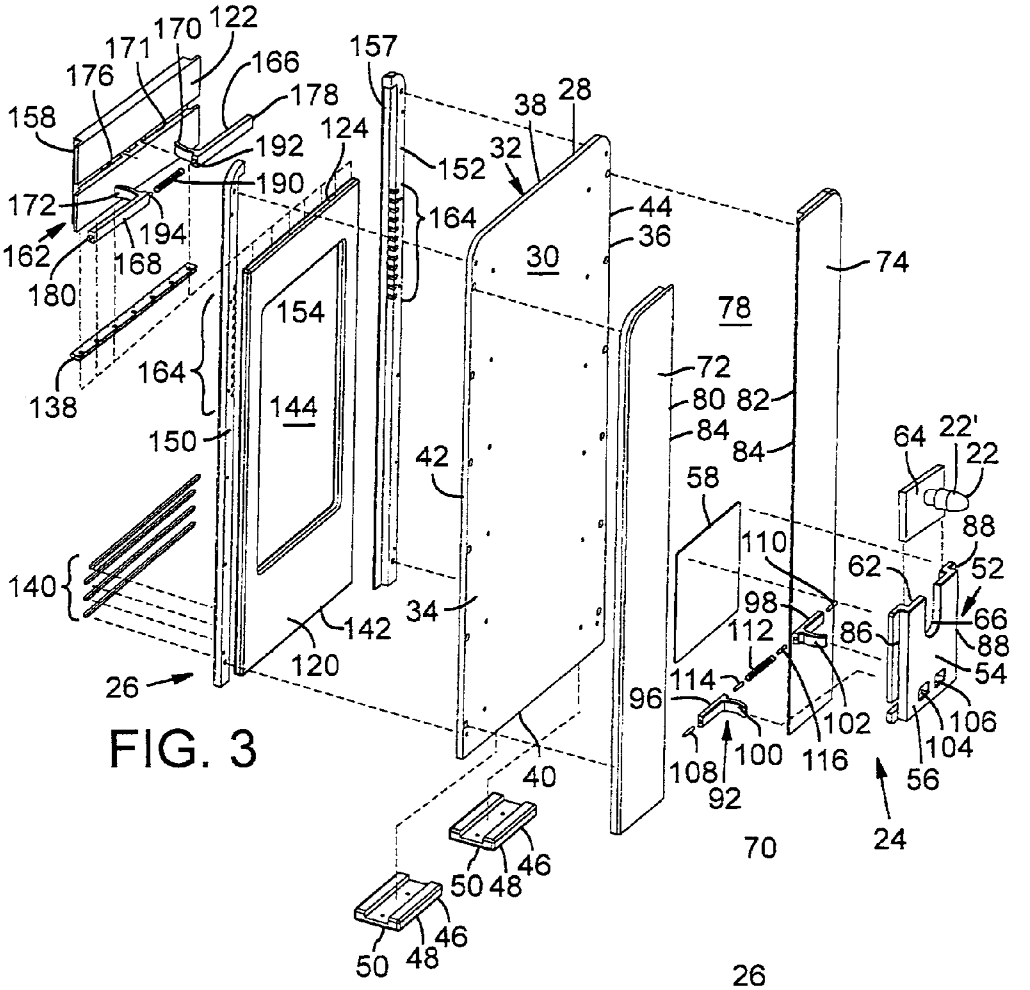
FIG. 3 is an exploded, isometric view of the phallic device mount of FIG. 1.

Referring to FIGS. 1 and 3, the mount 20 preferably includes a substantially planar base 28 defining a front side 30, back side 32, left side 34, right side 36, upper edge 38, lower edge 40, and left and right edges 42, 44, respectively. Feet 46, preferably having anti-slip material 48 such as rubber or the like on their lower sides 50, are secured to the lower edge 40 of the substantially planar base 28.

The phallic device mounting portion 24 includes a structure 52 for mounting a phallic device 22 such as a penis substitute, elongate sexual device, dildos, vibrators, or the like, thereto. Preferably, the phallic device mounting portion 24 includes a substantially planar front surface 54 with the phallic device 22 extending substantially perpendicular thereto. More preferably, the phallic device mounting portion 24 is substantially planar and includes a face member 56 and a substantially planar base member 58. The face member 56 is formed to define a recess 60 therein that is open along a top edge 62. The recess 60 is preferably sized to detachably receive a substantially planar base portion 64 of the phallic device 22. An opening 66 extending from the upper edge 38 of the face member 56 through the front surface 54 allows the phallic device 22 to extend therethrough.

Preferably, the phallic device 22 includes a universal mounting portion 22' that is detachably secured to the phallic device mounting portion 24, and a plurality of different phallic devices (not shown) each of which is adapted to be installed, one at a time, onto the universal mounting portion 22'. Such universal mounting portions 22' are known. One such universal mounting portion is disclosed in U.S. Pat. No. 5,127,396 to McAllister, the disclosure of which is hereby incorporated by reference.

The phallic device mounting portion 24 is preferably slidably secured to the front side 30 of the base 28. One possible sliding structure 70 includes positioning a left and right substantially planar member 72, 74, respectively, along the left and right sides 34, 36, respectively, of the substantially planar base 28 to define a substantially vertical channel 78 therebetween. The edges 80, 82 of the substantially planar members 72, 74, respectively, directed toward the channel 78 each include a lip 84, or flange, extending toward the channel 78. Mating recesses 86, 88 extending along the left and right sides of the phallic device mounting portion 24 slidably engage the lips 84 on the left and right substantially planar members 72, 74 thereby allowing the phallic device mounting portion 24 to slide substantially vertically in the direction of arrows 90 shown in FIG. 1.

Figure 4:
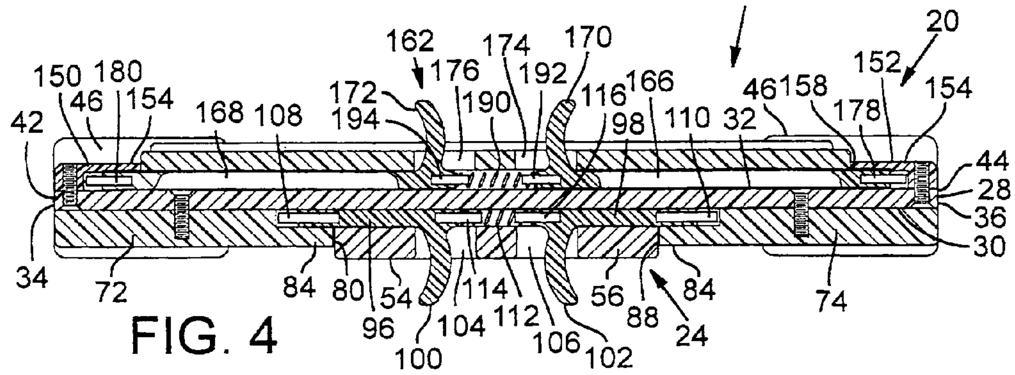
FIG. 4 is a cross sectional view of the phallic device mount of FIG. 1 taken along line 4—4 of FIG. 1.

Preferably, the phallic device mounting portion 24 includes a locking system 92 for allowing a user to select a desired height of the phallic device 22 relative to the base 28 and secure the phallic device mounting portion 24 at that height. One known locking system 92 is best shown in FIG. 3. The edges of the channel 78 include a plurality of vertically-aligned, spaced apart openings 94. The phallic device mounting portion 24 includes substantially horizontal levers 96, 98 slidably secured thereto with handle portions 100, 102, respectively, extending through parallel-aligned slots 104, 106 in the face member 56. Each lever 96, 98 includes a protrusion 108, 110, respectively, extending therefrom for matingly engaging one of the plurality of openings 94 in the edges of the channel 78. The levers 96, 98 are preferably biased to an extended position wherein the protrusions 108, 110 engage one of the openings 94. Such biasing is preferably accomplished with a spring 112 extending between the levers 96, 98 thereby urging them apart. More preferably, the spring 112 is operably secured to each lever 96, 98 by pins 114, 116 extending from each lever 96, 98 toward the spring 112 as best shown in FIG. 4.

A user adjusts the height of the phallic device mounting portion 24 by moving the handle portions 100, 102 of each lever 96, 98 towards each other, thereby disengaging the protrusions 108, 110 from their mating openings 94. The user slides the phallic device mounting portion 24 along the channel 78 to the desired height and then releases the handle portion 100, 102. The spring 112 urges the levers 96, 98 to extend the protrusions 108, 110 toward the edge of the channel 78. Accordingly, the protrusions 108, 110 are operably received within the adjacent openings 94 thereby securing the phallic device mounting portion 24 at the selected height.

The height adjustable bed mounting portion 26 preferably includes a substantially planar bed engaging portion 120 that is operably secured to a base engaging portion 122. Preferably, the base engaging portion 122 is slidably secured to the back side 32 of the base 28. More preferably, the bed engaging portion 120 is pivotally secured at a first end 124 to the base engaging portion 122 such that the bed mounting portion 26 moves with respect to the base 28 in the direction of arrows 126 (FIG. 1) to define a retracted position 130 (FIG. 2) in which the bed engaging portion 120 is positioned substantially parallel to and substantially adjacent to the base 28, and an in-use position 132 (FIG. 1) in which the bed engaging portion 120 is positioned substantially perpendicular to the base 28 as best shown in FIG. 1.

Even more preferably, the bed engaging portion 120 is pivotally secured to the base 28 with an elongate hinge 138, and anti-slip material 140, such as rubber or the like is positioned on the bed engaging portion 120 toward the opposite second end 142 of the bed engaging portion 120. In order to reduce the overall weight of the phallic device mount 20, the bed engaging portion 120 may also include a large opening 144 therein as best shown in FIG. 3.

One possible structure for slidably securing the base engaging portion 122 to the base 28 includes securing left and right rails 150, 152, respectively, each having a lip 154, or flange, extending therefrom to define a substantially vertical bed mounting portion channel 156 therebetween. Mating recesses 158 in the base engaging portion 122 operably engage the lips 154 thereby allowing the base engaging portion 122 to slide in the direction of arrows 160 (FIG. 1).

Preferably, the base engaging portion 122 includes a locking system 162 for allowing a user to select a desired height of the bed mounting portion 26 relative to the base 28 and then secure the base engaging portion 122 at that height. One known locking system 162 is best shown in FIG. 3. The rails 150, 152 include a plurality of vertically-aligned, spaced apart openings 164. The base engaging portion 122 includes substantially horizontal levers 166, 168 slidably secured thereto with handle portions 170, 172 extending through slots 174, 176 in the face of the base engaging portion 122. Each lever 166, 168 includes a protrusion 178, 180 extending therefrom for matingly engaging one of the plurality of openings 164. The levers 166, 168 are preferably biased to an extended position wherein the protrusions 178, 180 engage one of the openings 164. Such biasing is preferably accomplished with a spring 190 extending between the levers 166, 168 thereby urging them apart. More preferably, the spring 190 is operably secured to each lever 166, 168 by rods 192, 194 extending from each lever 166, 168 toward the spring 190 as best shown in FIG. 4.

A user adjusts the height of the bed mounting portion 26 by moving the handle portions 170, 172 of each lever 166, 168 towards each other, thereby disengaging the protrusions from their mating openings. The user slides the base engaging portion 122 to the desired height and then released the handle portions 170, 172. The spring 190 urges the levers 166, 168 to extend the protrusions 178, 180 toward the openings 164.

Accordingly, the protrusions 178, 180 are operably received within the adjacent openings 164 thereby securing the bed mounting portion 26 at the selected height.

B. Use and Operation

A user uses the phallic device mount 20 by attaching a phallic device 22 to the phallic device mounting portion 24 and positioning the base 28 substantially vertically next to a bed 200 as shown in FIG. 1. The user then adjusts the height of the bed mounting portion 26 so that the hinge 138 is substantially at the same height as a substantially horizontal surface 202 of the bed 200, such as the break between the box springs 204 and mattress 206. The user then moves the bed mounting portion 26 from its retracted position 130 (FIG. 2) to its in use position 132 (FIG. 1) and slides the bed engaging portion 120 between the box springs 204 and mattress 206 as shown thereby securing the base 28 to the bed 200. The weight of the mattress 206 on the bed engaging portion 120 combined with the anti-slip material 140 on the bed engaging portion 120 further secure the base 28 in place. The user then adjusts the height of the phallic device 22 by adjusting the phallic device mounting portion 24 to the desired vertical height.

Preferably, the channel 78 is sized so as to allow the phallic device 22 to be positioned substantially anywhere along the vertical length of the base 28 including being substantially close to the lower edge 40 of the base 28 and the upper edge 38 of the base 28. Accordingly, a user can use the phallic device 22 by either lying on their back on the floor adjacent to the phallic device mount 20, in which case the phallic device mounting portion 24 is positioned toward the lower edge 40 of the base 28, or by resting on all fours facing away from the phallic device mounting portion 24 such that their buttocks and/or vagina is aligned with the phallic device 22.

C. Additional Features and Embodiments

In view of the wide variety of embodiments to which the principles of the invention can be applied, it should be apparent that the detailed embodiments are illustrative only and should not be taken as limiting the scope of the invention. For example, the embodiment disclosed in FIGS. 1–4 discloses the base 28 and bed mounting portion 26 to be substantially rectangular. This allows the bed mounting portion 26 to be received within the base 28 for easy storage and concealment of the mount 20 when not in use. FIGS. 5–7 disclose different shaped structures. In this alternative embodiment, the base 28' is much narrower thereby allowing a user's legs to pass-by on either side easily during use. Also, the bed engaging portion 120' includes a flared outer portion 220, which preferably includes strips of anti-slip material 140 thereon, to thereby increase the surface area of the bed engaging portion 120' and improve the rigidity and stability of the mount 20' during use.

Also, as shown in FIGS. 8 & 9, the phallic device mounting portion 24 may be completely detached from the base 28 and used as a stand-alone phallic device mount. For example, a strap 260 can be secured to the phallic device 22 and wrapped around an auxiliary support structure 262, such as a door or the like, to allow a user additional opportunities to use their phallic device 22. In such case, the phallic device mount 20 can include one or more slots 264 for allowing the strap 260 to be passed therethrough. The strap 260 preferably includes securing structures such as a buckle or hook and loop material 266, thereby allowing a user to detachably secure just the phallic device mounting portion 24 to an auxiliary support structure 262.

Figure 2:
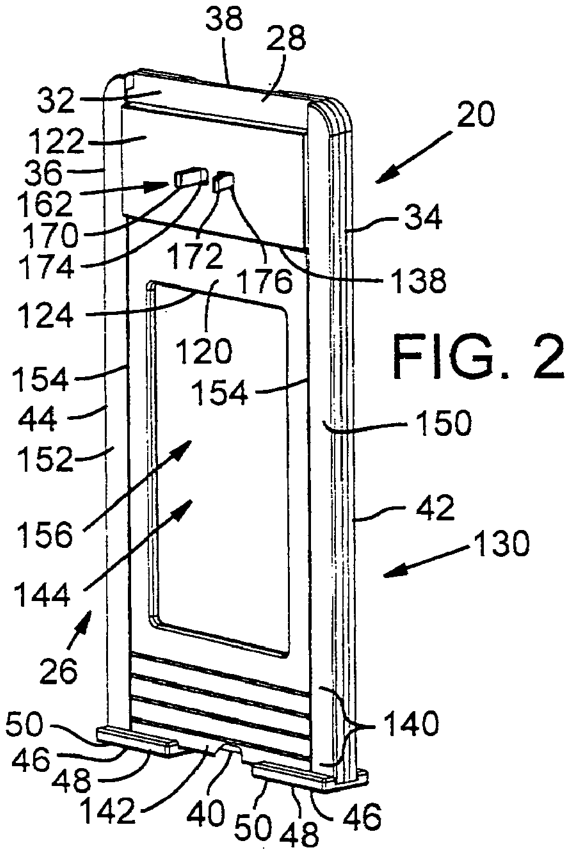
FIG. 2 is an isometric, back view of the phallic device mount structure of FIG. 1 showing a possible retracted position.

In addition, the phallic device mount 20 of the present invention may be used in other ways as well. For example, the base 28 may be positioned substantially horizontally extending between the seats of two chairs or the like or resting flat on a substantially horizontal surface such as a bed. In such case, the bed mounting portion 26 preferably remains in its retracted position 130 (FIG. 2).

In can appreciated that the mount 28 can also be used to assist paraplegics, quadriplegics, and others with conditions that limit their movement, to simulate normal sexual intercourse with a partner. The adjustability of the mount 28 allows the phallic device mounting portion to be laid over, on, under or attached to a wheelchair, hospital bed or other assistive device thereby allowing such individuals to engage in a large variety of sexual experiences. In addition, the mount 28 may stand alone to allow and individual with a disfiguring condition to simulate the experience of sexual intercourse without a partner.

In light of these additional embodiments and methods of use, the claimed invention includes all such modifications as may come within the scope of the following claims and equivalents thereto.

We claim:

1. A phallic device mount for operably securing a phallic device thereto, the phallic device mount supported by a bed having substantially planar mattress resting substantially horizontally thereon, said phallic device mount comprising:

a base having a bed-mounting portion and a phallic device-mounting portion;

said bed-mounting portion having a substantially horizontal portion positionable below the mattress so as to hold the base in place during use of the phallic device;

wherein said bed-mounting portion is slidably secured along a channel between said bed-mounting portion and said base, and said channel includes a plurality of spaced apart detents therealong; and a locking mechanism secured to said bed-mounting portion for operably engaging one detent of said plurality of spaced apart detents thereby holding said bed-mounting portion at a desired position along said channel.

2. The phallic device mount of claim 1, wherein said horizontal portion is substantially planar.

3. The phallic device mount of claim 1, wherein said substantially horizontal portion has an engaged position in which it is operably secured below the mattress, and a retracted position in which the substantially horizontal planar portion is retracted within said base.

4. The phallic device mount of claim 1, wherein said horizontal portion is pivotally secured to said base-mounting portion.

5. The phallic device mount of claim 1, wherein said bed-mounting portion is adjustable relative to said base such that the vertical position or the substantially horizontal portion may be adjusted.

6. The phallic device mount of claim 1, wherein said base is elongate and aligned substantially vertical.

7. The phallic device mount of claim 1, wherein said substantially horizontal portion includes anti-slip material thereon for gripping the mattress.

8. The phallic device mount of claim 1, wherein said phallic device-mounting portion includes a universal phallic device mount for detachably securing a phallic device thereto.

9. A phallic device mount for operably securing a phallic device thereto, the phallic device mount supported by a bed having a substantially planar mattress resting substantially horizontally thereon, said phallic device mount comprising:

a base having a bed-mounting portion and a phallic device-mounting portion;

said bed-mounting portion having a substantially horizontal portion positionable below the mattress so as to hold the base in place during use of the phallic device;

wherein said phallic device-mounting portion is slidably secured along a channel between phallic device-mounting portion and said base, and said channel includes a plurality of spaced apart detents therealong; and a locking mechanism secured to said phallic device-mounting portion for operably engaging one detent of said plurality of spaced apart detents thereby holding said phallic-device-mounting portion at a desired position along said channel.

10. The phallic device mount of claim 9, wherein said horizontal portion is substantially planar.

11. The phallic device mount of claim 9, wherein said substantially horizontal portion has an engaged position in which it is operably secured below the mattress, and a retracted position in which the substantially horizontal planar portion is retracted within said base.

12. The phallic device mount of claim 9, wherein said horizontal portion is pivotally secured to said base-mounting portion.

13. The phallic device mounting of claim 9, wherein said base-mounting portion is adjustable relative to said base such they the vertical position of the substantially horizontal portion may be adjusted.

14. A phallic device mount for operably securing a phallic device thereto, the phallic device mount supported by a bed having substantially planar mattress resting substantially horizontally thereon, said phallic device mount comprising:

a base having a bed-mounting portion and a phallic device-mounting portion;

said bed-mounting portion having a substantially horizontal portion positionable below the mattress so as to hold the base in place during use of the phallic device;

wherein said phallic device-mounting portion has substantially planar base portion and a face plate having a recess therein, said face plate spaced apart from said substantially planar base portion defining a gap therebetween so that a phallic device having a substantially planar base may be detachably secured to said phallic device mount by positioning said substantially planar base within said gap so that said phallic device extends through said recess in said face plate.

15. The phallic device mount of claim 14, wherein said substantially horizontal portion has an engaged position in which it is operably secured below the mattress, and a retracted position in which the substantially horizontal planar portion is retracted within said base.

16. The phallic device mount of claim 14, wherein said horizontal portion is pivotally secured to said base-mounting portion.

17. The phallic device mount of claim 14, wherein said base-mounting portion is adjustable relative to said base such that the vertical position of the substantially horizontal portion may he adjusted.

18. The phallic device mount of claim 14, wherein said phallic device-mounting portion is slidably secured to said base.

19. The phallic device mount of claim 14, wherein said phallic device mounting portion is detachably secured to said base.

* * * * *